(12) United States Patent
Tsuyuki

(10) Patent No.: US 11,607,114 B2
(45) Date of Patent: Mar. 21, 2023

(54) ENDOSCOPE, METHOD FOR ADJUSTMENT OF ENDOSCOPE, AND IMAGE PICKUP APPARATUS

(71) Applicant: OLYMPUS CORPORATION, Hachioji (JP)

(72) Inventor: Hiroshi Tsuyuki, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 736 days.

(21) Appl. No.: 16/583,124

(22) Filed: Sep. 25, 2019

(65) Prior Publication Data

US 2020/0015656 A1     Jan. 16, 2020

Related U.S. Application Data

(63) Continuation of application No. PCT/JP2018/009799, filed on Mar. 13, 2018.

(30) Foreign Application Priority Data

Apr. 3, 2017   (JP) .............................. JP2017-073886

(51) Int. Cl.
*G02B 27/14*   (2006.01)
*G02B 27/28*   (2006.01)
(Continued)

(52) U.S. Cl.
CPC ...... *A61B 1/00096* (2013.01); *A61B 1/00013* (2013.01); *A61B 1/000095* (2022.02);
(Continued)

(58) Field of Classification Search
CPC ...... G02B 23/04; G02B 23/243; G02B 23/26; G02B 21/00; G02B 21/0016;
(Continued)

(56) References Cited

U.S. PATENT DOCUMENTS 9,030,543 B2    5/2015 Tsuyuki et al.
10,893,793 B2 *  1/2021 Tsuyuki ............... A61B 1/0669
(Continued)

FOREIGN PATENT DOCUMENTS

JP     S62220919 A    9/1987
JP     H05164990 A    6/1993
(Continued)

OTHER PUBLICATIONS

International Search Report (ISR) dated Jun. 19, 2018 (and English translation thereof) issued in International Application No. PCT/JP2018/009799.

(Continued)

*Primary Examiner* — Thong Q Nguyen
(74) *Attorney, Agent, or Firm* — Holtz, Holtz & Volek PC

(57) ABSTRACT

An endoscope includes in order from an object side, an objective optical system, an optical-path splitter, an image sensor, and an image processor. A λ/4 wavelength plate is disposed between the objective optical system and the splitter. The splitter includes first and second prisms, and has a beam splitting surface at which the first prism and the second prism are brought into close contact. The splitter splits light at the beam splitting surface, into a first optical path through which P-polarized light is transmitted and a second optical path through which S-polarized light is reflected. The first and second prisms are slid relative to one another along the beam splitting surface to adjust optical path lengths of the first and second optical paths, and are disposed at positions to cancel an amount of shift in focusing positions of extraordinary and ordinary light, and satisfy specific conditional expressions.

20 Claims, 8 Drawing Sheets

(51) Int. Cl.
*A61B 1/00* (2006.01)
*G02B 23/04* (2006.01)
*G02B 23/26* (2006.01)
*G02B 23/24* (2006.01)

(52) U.S. Cl.
CPC ............ *G02B 23/04* (2013.01); *G02B 23/26* (2013.01); *G02B 23/243* (2013.01)

(58) Field of Classification Search
CPC ............ G02B 21/0028; G02B 21/0032; G02B 21/0056; G02B 21/006; G02B 21/0068; G02B 21/0072; G02B 5/00; G02B 5/04; G02B 27/0025; G02B 27/0075; G02B 27/10; G02B 27/1006; G02B 27/106; G02B 27/1073; G02B 27/126; G02B 27/28; G02B 27/283; G02B 27/286
USPC .......... 359/368–398, 483.1–494.1, 618–628, 359/618–640
See application file for complete search history.

(56) References Cited

U.S. PATENT DOCUMENTS

| | | | |
|---|---|---|---|
| 10,914,936 B2 * | 2/2021 | Tsuyuki | G02B 21/18 |
| 2003/0016325 A1 | 1/2003 | Konno et al. | |
| 2014/0176692 A1 | 6/2014 | Tsuyuki et al. | |

FOREIGN PATENT DOCUMENTS

| | | | |
|---|---|---|---|
| JP | 2003107477 A | | 4/2003 |
| JP | 2003307678 A | | 10/2003 |
| JP | 2005-292239 | * | 10/2005 |
| JP | 2009-14487 | * | 1/2009 |
| JP | 2012159784 A | | 8/2012 |
| JP | 2012216599 A | | 11/2012 |
| WO | 2008052405 A1 | | 5/2008 |
| WO | 2014002740 A1 | | 1/2014 |

OTHER PUBLICATIONS

Japanese Office Action dated Nov. 28, 2018 (and English translation thereof) issued in Japanese Patent Application No. JP 2018-549276.
Written Opinion of the International Searching Authority dated Jun. 19, 2018, issued in International Application No. PCT/JP2018/009799.
International Preliminary Report on Patentability (IPRP) dated Oct. 17, 2019 (and English translation thereof), Issued in International Application No. PCT/JP2018/009799.
Chinese Office Action (and English language translation thereof) dated Jan. 28, 2021 issued in Chinese Application No. 201880022874.3.

* cited by examiner

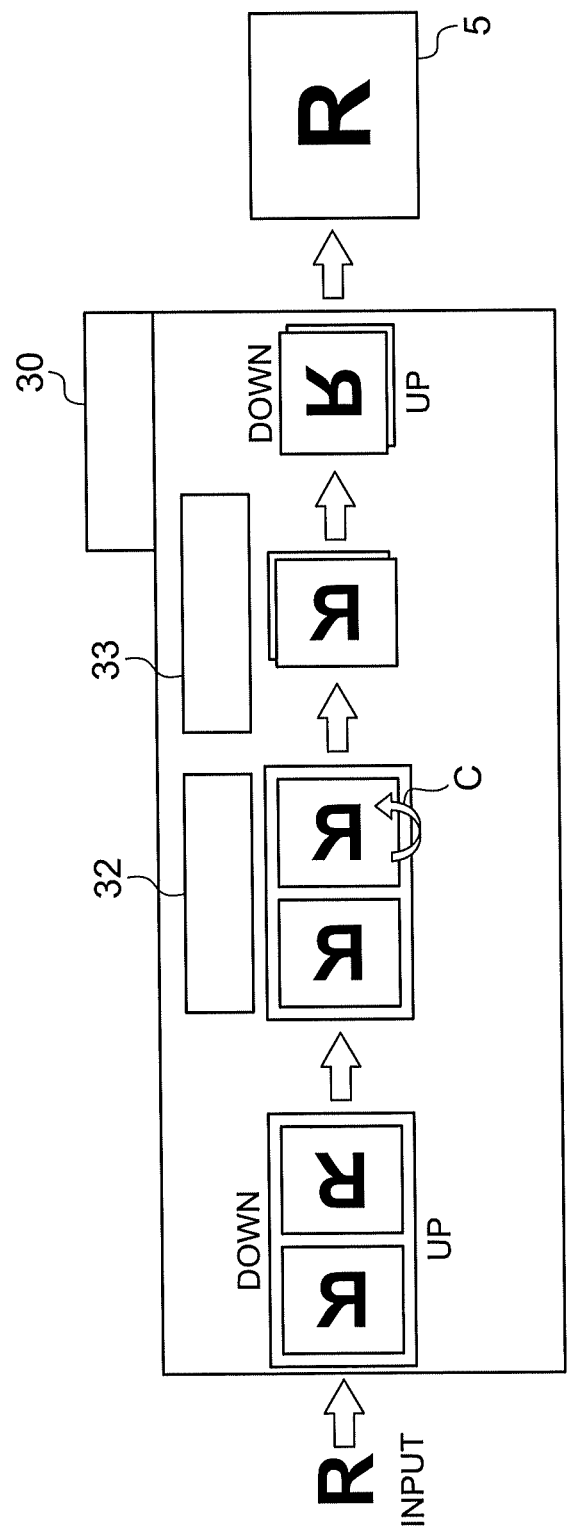

ENDOSCOPE, METHOD FOR ADJUSTMENT OF ENDOSCOPE, AND IMAGE PICKUP APPARATUS

CROSS-REFERENCE TO RELATED APPLICATION

The present application is a continuation application of PCT/JP2018/009799 filed on Mar. 13, 2018 which is based upon and claims the benefit of priority from Japanese Patent Application No. 2017-073886 filed on Apr. 3, 2017; the entire contents of which are incorporated herein by reference.

BACKGROUND

Technical Field

The disclosure relates to an endoscope, a method for adjustment of endoscope, and an image pickup apparatus.

Description of the Related Art

Generally, in an instrument including an image sensor, such as an endoscope system, it has been known that a depth of field narrows with an increase in the number of pixels of the image sensor. In other words, in an image sensor, as a pixel pitch (horizontal and vertical dimensions of one pixel) becomes small, since a diameter of a permissible circle of confusion also becomes small with the pixel pitch becoming small, a depth of field of an image pickup apparatus becomes narrow.

For widening the depth of field, an arrangement in which an image is divided and images are formed, and images acquired are combined by image processing and the depth is widened, has been proposed. Here, at the time of splitting the image, using an optical-path splitter in which polarization is used is effective. In the optical-path splitter in which polarization is used, it is desirable to make light which is depolarized by a λ/4 wavelength plate for instance, incident on the optical-path splitter.

In a λ/4 wavelength plate in which birefringence is used, a focusing position differs for ordinary light and extraordinary light. It has been disclosed in Japanese Patent Application Laid-open Publication No. 2003-307678, that it is possible to move a second prism along a coated surface of a first prism by a prism drive unit. Accordingly, a shift in position of an image forming surface due to a difference in a wavelength of visible light and a wavelength of infrared light is corrected.

Moreover, in International Unexamined Patent Application Publication No. 2014/002740, an arrangement for adjusting an optical path length by sliding a beam splitting surface has been disclosed.

SUMMARY

An endoscope according to at least some embodiments, includes in order from an object side, an objective optical system; and an optical-path splitter which splits light from the objective optical system into two, wherein a λ/4 wavelength plate made of a birefringent material is disposed in an optical path between the objective optical system and the optical-path splitter, and the optical-path splitter includes in order from the object side, a first prism and a second prism, and the optical-path splitter has a beam splitting surface at which the first prism and the second prism are brought into close contact, and the optical-path splitter splits light at the beam splitting surface into a first optical path through which P-polarized light is transmitted and a second optical path through which S-polarized light is reflected, and the first prism and the second prism, by sliding the beam splitting surface, adjust an optical path length of the first optical path and an optical path length of the second optical path, and the first prism and the second prism are disposed at positions of cancelling an amount of shift in a focusing position of extraordinary light and a focusing position of ordinary light occurred at the λ/4 wavelength plate having birefringence, and satisfy the following conditional expressions (1) and (2), $$0.01 < \Delta L \times npbs/Dy \leq 0.15 \qquad (1)$$

$$0.09 \leq d/|\Delta n| \leq 5.7 \qquad (2) \text{ (unit mm)}$$

where, $\Delta L$ denotes an amount of adjustment of a difference in the optical path length of the second optical path and the optical path length of the first optical path in the optical-path splitter (air conversion length), and here $$\Delta L = |\Delta L1 - \Delta L2|, \text{ where}$$

$\Delta L1$ denotes a difference in the optical path length (air conversion length) occurred due to a manufacturing error of the optical-path splitter, $\Delta L2$ denotes an amount of shift in the focusing position (air conversion length) occurred due to the λ/4 wavelength plate, $npbs$ denotes a refractive index for an e-line of the optical-path splitter, $Dy$ denotes a dimension of the optical-path splitter in a direction in which the first prism and the second prism of the optical-path splitter are orthogonal to an optical axis of the objective optical system, $d$ denotes a thickness of the λ/4 wavelength plate, and $\Delta n$ denotes a birefringence for the e-line of the λ/4 wavelength plate.

A method for adjustment of endoscope according to at least some embodiments, the endoscope includes in order from an object side, an objective optical system, and an optical-path splitter which splits light from the objective optical system into two, and a λ/4 wavelength plate made of a birefringent material is disposed in an optical path between the objective optical system and the optical-path splitter, and the optical-path splitter includes in order from the object side, a first prism and a second prism, and the optical-path splitter has a beam splitting surface at which the first prism and the second prism are brought into close contact, and the optical-path splitter splits the light at the beam splitting surface, into a first optical path through which P-polarized light is transmitted and a second optical path through which S-polarized light is reflected, the method includes:

sliding in which, a manufacturing error is adjusted by adjusting an optical path length of the first optical path and an optical path length of the second optical path by sliding the beam splitting surface; and cancelling in which, an amount of shift in a focusing position of extraordinary light and a focusing position of ordinary light occurred at the λ/4 wavelength plate having birefringence is cancelled, wherein the following conditional expressions (1) and (2) are satisfied.

$$0.01 < \Delta L \times npbs / Dy \leq 0.15 \quad (1)$$

$$0.09 \leq d/|\Delta n| \leq 5.7 \quad (2) \text{ (unit mm)}$$

where,

ΔL denotes an amount of adjustment of a difference in the optical path length of the second optical path and the optical path length of the first optical path in the optical-path splitter (air conversion length), and here $$\Delta L = |\Delta L1 - \Delta L2|, \text{ where}$$

ΔL1 denotes a difference in the optical path length (air conversion length) occurred due to a manufacturing error of the optical-path splitter, ΔL2 denotes an amount of shift in the focusing position (air conversion length) occurred due to the λ/4 wavelength plate, npbs denotes a refractive index for an e-line of the optical-path splitter, Dy denotes a dimension of the optical-path splitter in a direction in which the first prism and the second prism of the optical-path splitter are orthogonal to an optical axis of the objective optical system, d denotes a thickness of the λ/4 wavelength plate, and Δn denotes a birefringence for the e-line of the λ/4 wavelength plate.

An image pickup apparatus according to at least some embodiments, the image pickup apparatus includes an image sensor. The image pickup apparatus includes, in order from an object side, an objective optical system; and an optical-path splitter which splits light from the objective optical system into two, wherein a λ/4 wavelength plate made of a birefringent material is disposed in an optical path between the objective optical system and the optical-path splitter, and the optical-path splitter includes in order from the object side, a first prism and a second prism, and the optical-path splitter has a beam splitting surface at which the first prism and the second prism are brought into close contact, and the optical-path splitter splits the light at the beam splitting surface, into a first optical path through which P-polarized light is transmitted and a second optical path through which S-polarized light is reflected, and the first prism and the second prism, by sliding the beam splitting surface, adjust an optical path length of the first optical path and an optical path length of the second optical path, and are disposed at positions of cancelling an amount of shift in a focusing position of extraordinary light and a focusing position of ordinary light occurred at the λ/4 wavelength plate having birefringence, and the following conditional expressions (1) and (2) are satisfied.

$$0.01 < \Delta L \times npbs / Dy \leq 0.15 \quad (1)$$

$$0.09 \leq d/|\Delta n| \leq 5.7 \quad (2) \text{ (unit mm)}$$

where,

ΔL denotes an amount of adjustment of a difference in the optical path length of the second optical path with respect to the first optical path in the optical-path splitter (air conversion length), and here $$\Delta L = |\Delta L1 - \Delta L2|, \text{ where}$$

ΔL1 denotes a difference in the optical path length (air conversion length) occurred due to a manufacturing error of the optical-path splitter, ΔL2 denotes an amount of shift in the focusing position (air conversion length) occurred due to the λ/4 wavelength plate, npbs denotes a refractive index for an e-line of the optical-path splitter, Dy denotes a dimension of the optical-path splitter in a direction in which the first prism and the second prism of the optical-path splitter are orthogonal to an optical axis of the objective optical system, d denotes a thickness of the λ/4 wavelength plate, and Δn denotes a birefringence for the e-line of the λ/4 wavelength plate.

BRIEF DESCRIPTION OF THE DRAWINGS

FIG. 9 is a diagram showing an image forming state in a case in which an image is formed on the image sensor after reflecting for the odd number of times by a beam splitter, in the endoscope system according to the embodiment; FIG. 10A is a cross-sectional view in a normal observation state, and FIG. 10B is a cross-sectional view in a close observation state.

DETAILED DESCRIPTION

Examples of an endoscope, a method for adjustment of endoscope, and an image pickup apparatus will be described below in detail with reference to the accompanying diagrams. However, the present invention is not restricted to the examples described below.

Figure 1:
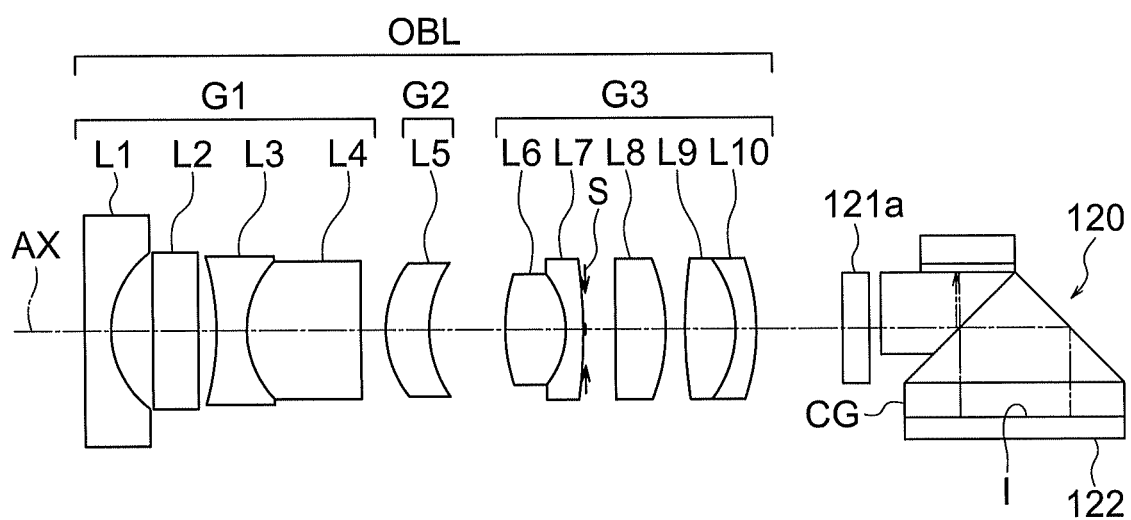
FIG. 1 is a cross-sectional view showing an arrangement of an objective optical system, an optical-path splitter, and an image sensor in an endoscope (image pickup apparatus) according to an embodiment(normal observation state)
Figure 2:
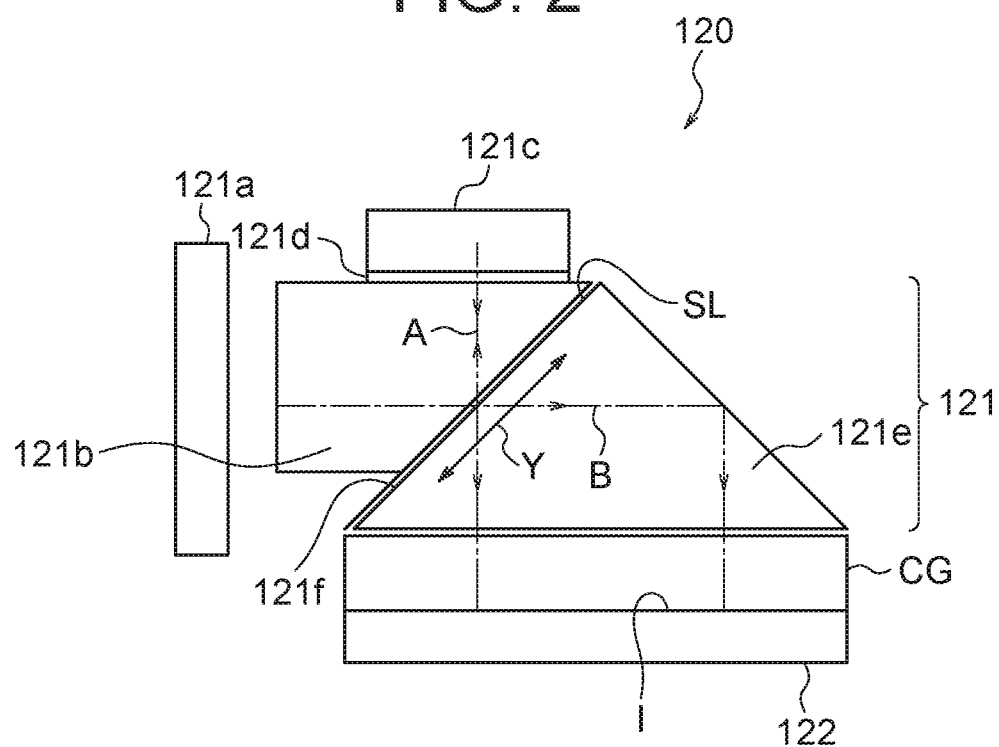
FIG. 2 is a schematic block diagram of a l/4 wavelength plate, the optical-path splitter, and the image sensor in the endoscope (image pickup apparatus) according to the embodiment.

FIG. 1 is a cross-sectional view showing an arrangement of an objective optical system OBL, an optical-path splitter 120, and an image sensor 122 in an endoscope (image pickup apparatus) according to an embodiment. Moreover, FIG. 2 is a schematic block diagram of a λ/4 wavelength plate 121a, the optical-path splitter 120, and the image sensor 122 in the endoscope according to the embodiment. The endoscope includes in order from an object side, an objective optical system OBL, an optical-path splitter 120 which splits light from the objective optical system OBL into two, an image sensor 122 which picks up two split images, and an image processor 30 (FIG. 7) having an image combining section combining the images picked up by the image sensor to one image. A λ/4 wavelength plate 121a made of a birefringent material is disposed in an optical path between the objective optical system OBL and the optical-path splitter 120. The optical-path splitter 120 includes in order from the object side, a first prism 121b and a second prism 121e, and has a beam splitting surface SL at which the first prism 121b and the second prism 121e are brought into close contact and glued. The optical-path splitter 120 splits light at the beam splitting surface SL, into a first optical path B through which P-polarized light is transmitted and a second optical path A through which S-polarized light reflected. The first prism 121b and the second prism 121e, by sliding the beam splitting surface SL, adjust an optical path length of the first optical path B and an optical path length of the second optical path A, and are disposed at positions of cancelling an amount of shift in a focusing position of extraordinary light and a focusing position of ordinary light occurred at the λ/4 wavelength plate 121a having birefringence, and the following conditional expressions (1) and (2) are satisfied.

$$0.01 < \Delta L \times npbs/Dy \leq 0.15 \quad (1)$$

$$0.09 \leq d/|\Delta n| \leq 5.7 \quad (2) \text{ (unit mm)}$$

where,

ΔL denotes an amount of adjustment of a difference in the optical path length of the second optical path A and the optical path length of the first optical path B in the optical-path splitter 120 (air conversion length), and here $$\Delta L = |\Delta L1 - \Delta L2|, \text{ where}$$

ΔL1 denotes a difference in the optical path length (air conversion length) occurred due to a manufacturing error of the optical-path splitter 120, ΔL2 denotes an amount of shift in the focusing position (air conversion length) occurred due to the λ/4 wavelength plate 121a, npbs denotes a refractive index for an e-line of the optical-path splitter 120, Dy denotes a dimension of the optical-path splitter 120 in a direction in which the first prism 121b and the second prism of the optical-path splitter 121e are orthogonal to an optical axis of the objective optical system OBL, d denotes a thickness of the λ/4 wavelength plate 121a, and Δn denotes a birefringence for the e-line of the λ/4 wavelength plate 121a.

Firstly, an arrangement of the optical-path splitter 120 will be described below by referring to FIG. 2. FIG. 2 is a diagram showing a schematic arrangement of the λ/4 wavelength plate 121a, the optical-path splitter 120, and the image sensor 122.

Light emerged from the objective optical system OBL is incident on the optical-path splitter 120 via the λ/4 wavelength plate 121a. The λ/4 wavelength plate 121a shows an effect of depolarizing polarized light.

The optical-path splitter 120 includes a polarization beam splitter 121 which splits an object image into two optical images of different focus, and the image sensor 122 which acquires two images by picking up the two optical images.

As shown in FIG. 2, the polarization beam splitter 121 includes the first prism 121b on the object side, the second prism 121e on an image side, a mirror 121c, and a λ/4 plate sheet 121d. Both the first prism 121b on the object side and the second prism 121e on the image side have the beam splitting surface SL which is inclined at 45 degrees with respect to an optical axis AX.

A polarization splitting film 121f is formed on the beam splitting surface SL of the first prism 121b on the object side. Moreover, the first prism 121b on the object side and the second prism 121e form the polarization beam splitter 121 by the beam splitting surface SL brought in close contact via the polarization splitting film 121f.

Moreover, the mirror 121c is provided near an edge surface of the first prism 121b on the object side via the λ/4 plate sheet 121d. The image sensor 122 is attached to the edge surface of the second prism 121e on the image side via a cover glass CG. Here, I is an image forming surface (image pickup surface).

An object image from the objective optical system OBL is split into a P-polarized component (transmitted light) and an S-polarized component (reflected light) by the polarization splitting film 121f provided to the beam splitting surface SL of the first prism 121b on the object side, and is split into two optical images which are an optical image on a reflected-light side and an optical image on a transmitted-light side.

The optical image of the S-polarized component is reflected to a side facing the image sensor 122 at the polarization splitting film 121f and travels the second optical path A, and upon being transmitted through the λ/4 plate sheet 121d, is reflected at the mirror 121c, and is returned toward the image sensor 122. An angle of polarization of the optical image is turned through 90° by being transmitted once again through the λ/4 plate sheet 121d, and upon being transmitted through the polarization splitting film 121f, is formed as an image on the image sensor 122.

The optical image of the P-polarized component is transmitted through the polarization splitting film 121f and travels the first optical path B, and upon being reflected at a mirror surface provided to an opposite side of the beam splitting surface SL of the second prism 121e on the image side returning perpendicularly toward the image sensor 122, is formed as an image on the image sensor 122. At this time, an optical path in glass of prism is set such that there is a predetermined optical path difference of tens of μm for example between the second optical path A and the first optical path B, and the two optical images with different focus are formed on a light-receiving surface of the image sensor 122.

In other words, the first prism 121b on the object side and the second prism 121e on the image side are disposed such that an optical path length of the reflected-light side becomes shorter (smaller) than an optical path length (path length in glass) of the transmitted-light side reaching the image sensor 122 in the first prism 121b on the object side such that it is possible to split the object image into two optical images having different focusing positions. Here, the first prism 121b and the second prism 121e may be disposed such that the optical-path lens becomes longer (larger) contrary to the abovementioned case. At this time, an arrangement of a far-point image and a near-point image on the image sensor becomes reverse.

Figure 3:
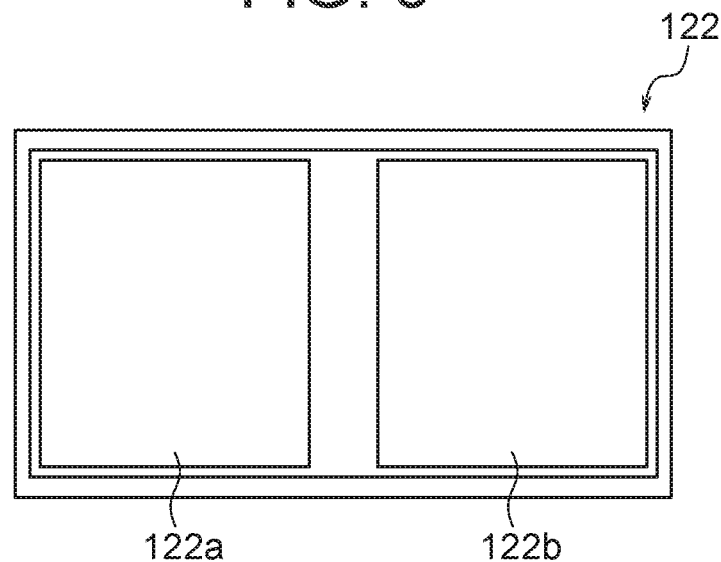
FIG. 3 is a schematic block diagram of the image sensor in the endoscope (image pickup apparatus) according to the embodiment.

FIG. 3 is a schematic block diagram of the image sensor 122. As shown in FIG. 3, the image sensor 122 is provided with two light-receiving areas (effective pixel areas) 122a and 122b in an overall pixel area of the image 122 in order to receive and pickup separately the two optical images with different focusing positions.

Figure 4:
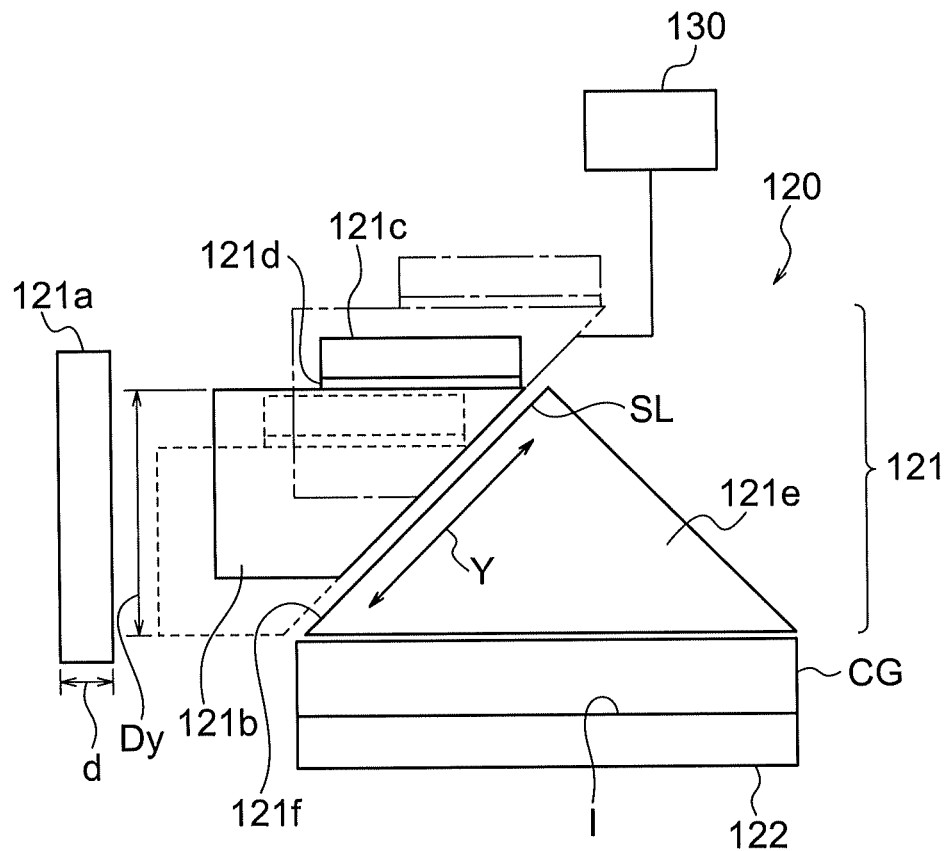
FIG. 4 is a diagram explaining a method for adjustment of the λ/4 wavelength plate, the optical-path splitter, and the image sensor in the endoscope (image pickup apparatus) according to the embodiment.

FIG. 4 is a diagram for explaining a method for adjustment of the λ/4 wavelength plate, the optical-path splitter, and the image sensor in the endoscope (image pickup apparatus). A prism drive unit 130 drives the first prism 121b and the second prism 121e relatively. For example, the prism drive unit 130 is a motor or an actuator. Accordingly, it is possible to slide the beam splitting surface SL along a direction of an arrow Y.

Next, an action and an effect of the present embodiment will be described below. In the present embodiment, for depolarizing a polarization state, the I/4 wavelength plate 121a in which a birefringent material is used, as mentioned above, is used. Here, as shown in FIG. 5, when the birefringence of the I/4 wavelength plate 121a in which the birefringent material is used becomes high, a shift ΔL2 occurs in a focusing position P1 of ordinary light Ray1 out of light incident light Ray and a focusing position of extraordinary light Ray2 out of light incident light Ray, and is not preferable.

Figure 5:
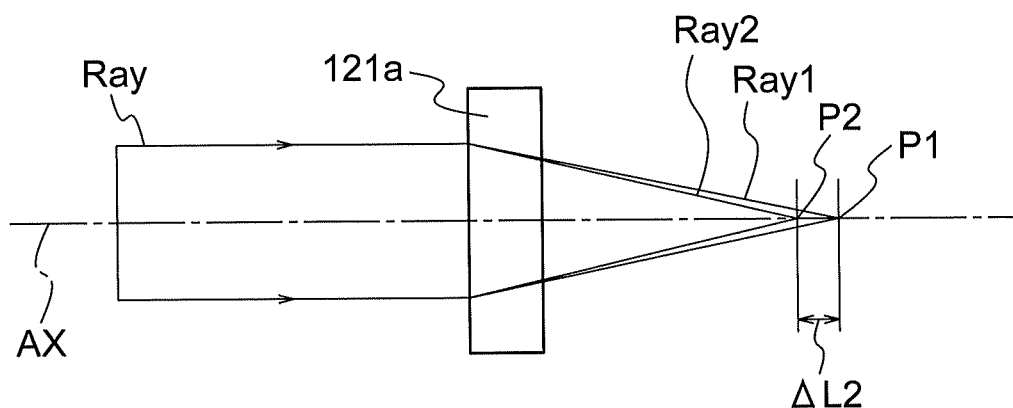
FIG. 5 is a diagram showing a focusing position of an extraordinary light ray and a focusing position of an ordinary light ray by the λ/4 wavelength plate.

FIG. 5 shows the focusing position of the ordinary light Ray 1 and the focusing position of the extraordinary light Ray 2 by the λ/4 wavelength plate 121a.

Therefore, by sliding the beam splitting surface SL of the polarization beam splitter and correcting the shift in the image forming position by adjusting an optical path length of the ordinary light (≈S-polarized light=second optical path A) and an optical path length of the extraordinary light (≈P-polarized light=first optical path B), it is possible to achieve a desired difference in the optical path lengths. A specific method for adjustment will be described later as a method for adjustment of endoscope system.

By sliding the beam splitting surface SL in the direction of the arrow Y (FIG. 4), or in other words, by adjusting the first prism 121b and the second prism 121e by sliding relatively, the difference in the optical path length of the ordinary light and the optical path length of the extraordinary light is corrected. Here, when the sliding adjustment is excessively large, the endoscope front-end portion which includes the objective optical system OBL becomes large in size and a shape after the sliding adjustment is deviated substantially from a designed shape, thereby leading to a possibility of weakening of a temperature and humidity resistance and an impact resistance.

Conditional expression (1) regulates so that an amount of sliding adjustment does not become larger than necessary. Restricting the amount of sliding adjustment to 15% or less of dimensions of an outer shape of the prism is desirable.

Moreover, conditional expression (2) is an expression which regulates ΔL in conditional expression (1). More specifically, conditional expression (2) restricts the ΔL2 which is determined by a relationship of the birefringence Δn of the λ/4 wavelength plate 121a and the thickness d of the λ/4 wavelength plate 121a. Moreover, ΔL is to be controlled not to become smaller or larger than necessary.

When a value falls below a lower limit value of conditional expression (2), a small amount of sliding adjustment serves the purpose. However, the depolarization effect becomes excessively small.

When an upper limit value of conditional expression (2) is exceeded, the amount of shift in focus ΔL2 becomes excessively large, thereby a size of the abovementioned endoscope front-end portion becoming large and an asymmetry of the sub-assembly of prisms after the adjustment becoming high, which leads to instability from resistance point of view.

The endoscope (image pickup apparatus) is an endoscope intended for widening a depth of field. For widening the depth of field, it is necessary to generate a predetermined difference in the optical path length of the far-point image and the near-point image after splitting the optical path by the polarization beam splitter as it will be described later. Therefore, the shift in the image forming position occurred due to the birefringence is corrected by the sliding adjustment, and a target value of a range of the depth of field is achieved.

In other application examples such as an endoscope intended for a 3D observation (stereoscopic observation) and widening a dynamic range, by carrying out an adjustment for making the difference in the optical path length zero, it is possible to achieve a favorable combined image.

Moreover, according to a preferable aspect of the present embodiment, it is desirable that the birefringent material of the λ/4 wavelength plate is one of LiNbO$_3$ (lithium niobate), YVO$_4$ (yttrium orthovanadate), calcite, and α-BBO (α-barium borate).

For achieving an effective depolarization effect, it is desirable to use a crystalline material having a high birefringence.

Moreover, according to another aspect of the present embodiment is a method for adjustment of endoscope. The endoscope includes in order from an object side, the objective optical system OBL, the optical-path splitter 120 which splits light from the objective optical system OBL in to two, the image sensor 122 which picks up the two split images, and an image processor 30 (FIG. 7) having an image combining unit which combines the images picked by the image sensor 122 and forms one image.

The λ/4 wavelength plate 121a made of a birefringent material is disposed in an optical path between the objective optical system OBL and the optical-path splitter 120.

The optical-path splitter 120 includes in order from the object side, the first prism 121b and the second prism 121e.

The optical-path splitter 120 has a beam splitting surface at which the first prism 121b and the second prism 121e are brought into close contact and glued.

The optical-path splitter 120 splits the light at the beam splitting surface SL, in to the first optical path B through which P-polarized light is transmitted and the second optical path A through which S-polarized light is reflected. The method includes steps of, sliding in which, a manufacturing error is adjusted by adjusting the optical path length of the first optical path B and the optical path length of the second optical path A by sliding the beam splitting surface SL (step S201 in FIG. 6), and cancelling in which, an amount of shift ΔL2 in a focusing position P2 of extraordinary light Ray2 and a focusing position P1 of ordinary light Ray1 occurred at the λ/4 wavelength plate 121a having birefringence is cancelled (step S202 in FIG. 6).

Figure 6:
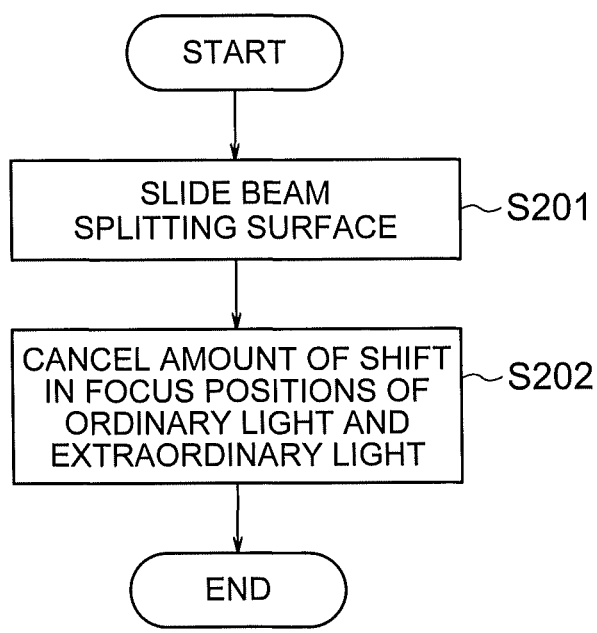
FIG. 6 is a flowchart showing a method for adjustment of the endoscope.

FIG. 6 is a flowchart showing the method for adjustment of endoscope.

Furthermore, according to a preferable aspect of the present embodiment, in the method for adjustment of endoscope, it is preferable that the following conditional expressions (1) and (2) are satisfied.

$$0.01 < \Delta L \times npbs/Dy \leq 0.15 \quad (1)$$

$$0.09 \leq d/|\Delta n| \leq 5.7 \quad (2)$$

where,

ΔL denotes an amount of adjustment of a difference in the optical path length of the second optical path and the optical path length of the first optical path in the optical-path splitter 120 (air conversion length), and here $$\Delta L = |\Delta L1 - \Delta L2|, \text{ where}$$

ΔL1 denotes a difference in the optical path length (air conversion length) occurred due to a manufacturing error of the optical-path splitter 120, ΔL2 denotes an amount of shift in the focusing position (air conversion length) occurred due to the λ/4 wavelength plate 121a, npbs denotes a refractive index for an e-line of the optical-path splitter 120, Dy denotes a dimension of the optical-path splitter 120 in a direction in which the first prism 121b and the second prism 121e of the optical-path splitter 120 are orthogonal to an optical axis AX of the objective optical system OBL, d denotes a thickness of the λ/4 wavelength plate 121a, and Δn denotes a birefringence for the e-line of the λ/4 wavelength plate 121a.

Technical significance of conditional expressions (1) and (2) in the method for adjustment of endoscope is same as the technical significance of conditional expressions (1) and (2) in the endoscope.

Next, a specific method for adjusting an optical path length will be described below. The optical path length is to be adjusted at the time of gluing a sub-assembly in which the first prism 121b and a mirror unit (mirror 121c and the λ/4 wavelength plate sheet 121d) are glued, and the second prism 121e.

The description will be made by citing an example of an optical system for widening the depth of field. In a case in which the difference in the optical path length of the first optical path B of a far-point focus image and the optical path length of the second optical path A of a near-point focus image is 50 μm for example, at least one of the first prism 121b and the second prism 121e is to be slid along the beam splitting surface SL such that the optical path length difference becomes 50 μm.

An actual amount of adjustment is determined by taking into consideration an accuracy of components of the polarization beam splitter 121 and the manufacturing error at the time of adjustment. In the present embodiment, the amount of adjustment is ΔL. In the polarization beam splitter 121 of the present embodiment, the optical path is split such that the P-polarized light travels through the first optical path B and the S-polarized light travels through the second optical path A.

A completed form as an optical system for endoscope is an arrangement in which the objective optical system OBL and the λ/4 wavelength plate 121a are combined. When a birefringent material is used for the λ/4 wavelength plate 121a, the amount of shift (difference) ΔL2 in an image forming position of the ordinary light and an image forming position of the extraordinary light occurs according to a magnitude of birefringence and a plate thickness.

In the polarization beam splitter 121, the ordinary light is split to the second optical path A, and the extraordinary light is split to the first optical path B. Therefore, in a process of adjusting the optical path length in which the prism unit is assembled, without taking into consideration the amount of shift ΔL2, it is not possible to achieve desired effect of widening the depth of field.

In other words, it is necessary to make |ΔL1−ΔL2|=ΔL the final amount of adjustment of the difference in the optical path lengths. In a case of an example 1 that will be described later, ΔL1 being 50 μm and ΔL2 (image forming position no-image forming position ne) being −7.3 μm, ΔL becomes 57.3 μm. In such manner, when −7.3 μm of ΔL2 is not anticipated, the difference in the optical path lengths becomes shorter than the target value.

Here, ΔL is an air-conversion length, and the real amount of sliding is determined by a practical refractive index of the polarization beam splitter 121. For instance, S-BSM18 (manufactured by OHARA Corporation) is used as a glass in a polarization beam splitter 121 of the example 1. The refractive index for the e-line is 1.64129. Therefore, the practical amount of adjustment is 57.3×1.64129≈94 μm.

On the other hand, since the amount of adjustment ΔL has an effect on a size of a front-end portion of the endoscope including an optical-path splitter, the practical amount of adjustment is limited. In the present embodiment, as shown in FIG. 4, regarding conditional expression (1), it is desirable to optimize with a proportion to an initial dimension Dy in a direction of sliding adjustment of the polarization beam splitter 121.

Since ΔL2 changes largely according to the plate thickness d and the birefringence Δn of the λ/4 wavelength plate 121a which is used, it is desirable to fit ΔL within a range of conditional expression (2).

It is most desirable that a crystal axis of the λ/4 wavelength plate 121a made of a birefringent material is perpendicular to an optical axis of the objective optical system OBL. Moreover, in a crystal with an inclined crystal axis, there occurs a low-pass effect. In other words, a point-splitting in which a low frequency which is lower than Nyquist frequency occurs and a resolution is degraded. Even when a manufacturing variation of the λ/4 wavelength plate is taken into consideration, it is desirable that a splitting width of an image is not more than 0.5 pixel with respect to a pixel size of an image sensor that is used.

Figure 7:
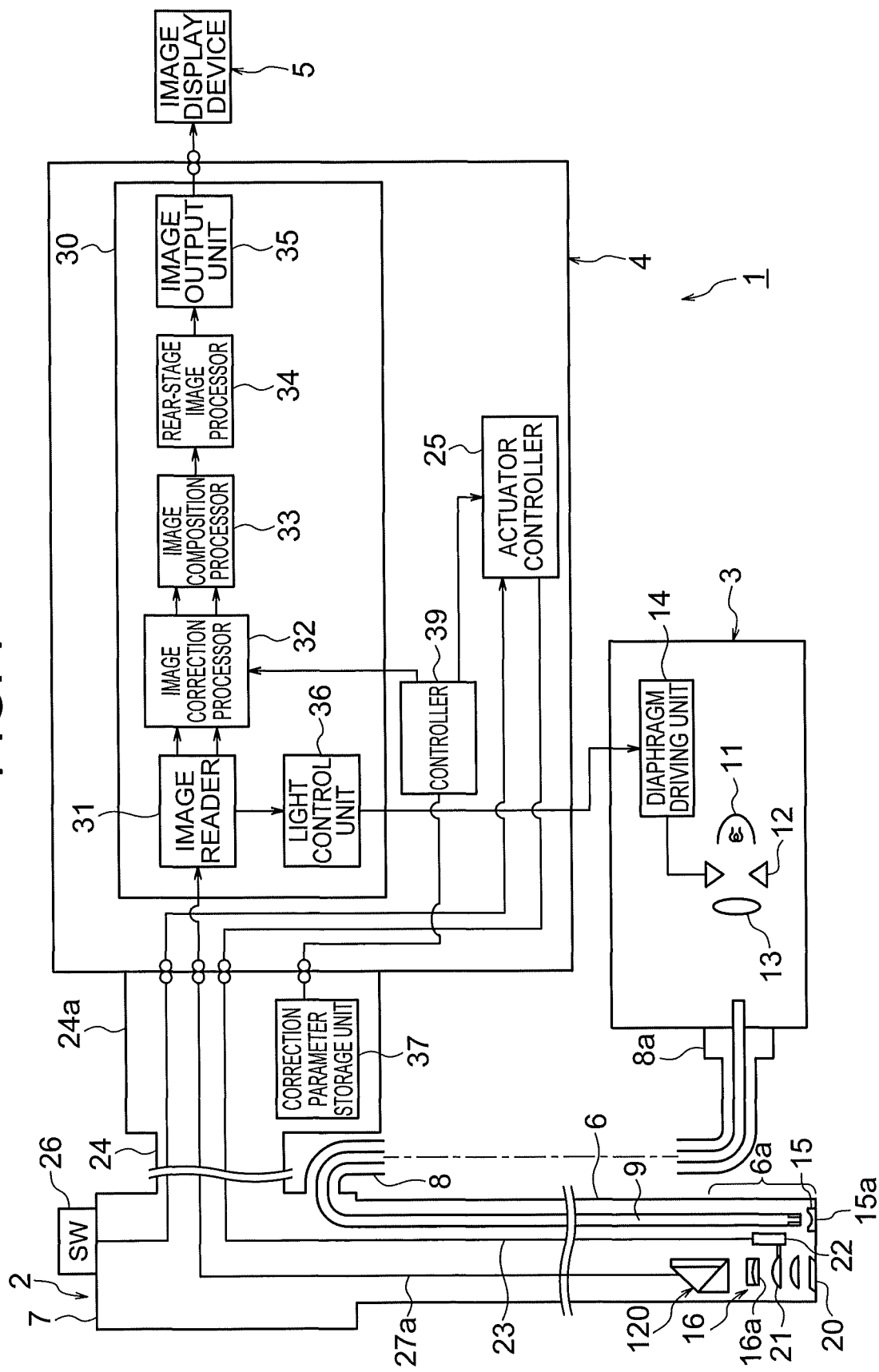
FIG. 7 is a functional block diagram showing an arrangement of an endoscope system according to the embodiment.

As illustrated in FIG. 7, an endoscope system 1 according to the present embodiment includes an endoscope 2 inserted into a subject, a light source 3 configured to supply illumination light to the endoscope 2, a processor 4, and an image display device 5.

The processor 4 has a function of performing image processing, but also has other functions. The processor 4 includes an actuator controller 25, an image processor 30, and a controller 39. The image display device 5 displays an image signal generated with the processor 4 as an endoscope image.

The endoscope 2 includes an elongated insertion unit 6 to be inserted into the subject, and an operating unit 7 provided at the rear end of the insertion unit 6. A light guide cable 8 extends outward from the operating unit 7. One end of the light guide cable 8 is detachably connected with the light source 3 through a connection unit 8a. The light guide cable 8 includes a light guide 9 therein. Part of the light guide 9 is disposed inside the insertion unit 6.

The light source 3 includes therein a lamp 11, such as a xenon lamp, as the light source. The light source is not limited to the lamp 11, such as a xenon lamp, but a light emitting diode (abbreviated to "LED") may be used. The transmitted light quantity of the illumination light generated with the lamp 11, for example, white light, is regulated with a diaphragm 12. Thereafter, the illumination light is condensed with a condenser lens 13, and made incident on an incident end surface of the light guide 9. It is possible to change the aperture of the diaphragm 12 with a diaphragm driving unit 14.

The light guide 9 transmits the illumination light generated by the light source 3 to a distal end portion 6a of the insertion unit 6. The transmitted illumination light is emitted from the distal end surface of the light guide 9. An illumination lens 15 is disposed in the distal end portion 6a while facing the distal end surface. The illumination lens 15 emits the illumination light from an illumination window 15a. In this manner, the observation target region inside the subject is illuminated.

An observation window 20 is provided adjacent to the illumination window 15a in the distal end portion 6a. Light from the observation target region passes through the observation window 20, and is made incident on the inside of the distal end portion 6a. The objective optical system is disposed behind the observation window 20. The objective optical system is formed of a lens group 16 and an optical path splitter 120.

The lens group 16 includes a lens 16a and a lens 21. The lens 21 is movable along the optical axis. In this manner, focusing is performed. An actuator 22 is disposed to move the lens 21.

One image sensor 122 (not illustrated) is disposed on the optical path splitter 120. Two optical images are simultaneously formed on the light-receiving surface of the image sensor 122. The two optical images are imaged with the image sensor 122.

The operating unit 7 is connected with the processor 4 through a cable 24. A signal connector 24a is provided in a portion connected with the processor 4. Transmission of various types of information is performed between the endoscope 2 and the processor 4 through the cable 24. The signal connector 24a includes a correction parameter storage unit 37.

The correction parameter storage unit 37 stores therein correction parameters (or information of correction parameters) used for correction of the image. The correction parameters are different between individual endoscopes. It is assumed that an endoscope having unique endoscope identification information is connected with the processor 4. In this case, on the basis of the endoscope identification information, correction parameters peculiar to the connected endoscope are read from the correction parameter storage unit 37. Image correction is performed in an image correction processor 32 on the basis of the read correction parameters. Presence/absence of correction is determined by the controller 39.

Control of the actuator 22 is performed by the actuator controller 25. For this reason, the actuator 22 and the actuator controller 25 are connected through a signal line 23. Moreover, the image sensor is connected with the image processor 30 through a signal line 27a. The signal from the image sensor is input to the image processor 30. Information of a switch 26 provided in the operating unit 7 is also transmitted to the processor 4 through a signal line.

When the optical path length in the first optical path B is slightly different from the optical path length in the second optical path A, two optical images in focus are formed in front of and behind the image pickup surface. The shift quantities of the optical images from the image pickup surface are slight. For this reason, two optical images in focus only in a part of the region are formed on the image pickup surface.

The two optical images are imaged with the image sensor 122. An image signal acquired by imaging is input to the image processor 30 through the signal line 27a. The image processor 30 includes an image reader 31, the image correction processor 32, an image composition processor 33, a rear-stage image processor 34, an image output unit 35, and a light control unit 36.

In the image reader 31, image signals of a plurality of images are read from the input image signal. Herein, both the number of optical images and the number of images is two.

In the optical system forming two optical images, a geometrical difference may occur. Examples of the geometrical difference include a relative shift (difference) of the two optical images, such as a shift (difference) in magnification, a shift (difference) in position, and a shift (difference) in rotational direction. It is difficult to completely remove these differences in manufacturing of the objective optical system or the like. However, when the shift quantities of them increase, for example, a composite image looks double. For this reason, it is preferable to correct the geometrical difference described above in the image correction processor 32.

The image correction processor 32 performs image correction on the two read images. The image correction processor 32 performs, for example, processing to make at least one difference among a relative difference in magnification, a difference in position, and a difference in rotation agree between the two images.

In addition, the image correction processor 32 performs tone correction. For this reason, the image correction processor 32 includes a tone correction unit (not illustrated). In tone correction, the tone correction unit performs processing to make relative luminance and saturation of the two images substantially agree in at least one desired specific wavelength band. The tone correction may be performed by the image correction processor 32, without providing the tone correction unit.

The image correction processor 32 changes the luminance in one of the two images to substantially agree with the luminance in the other image. Moreover, the image correction processor 32 changes the saturation in one of the images to substantially agree with the saturation in the other image.

As described above, in a method of acquiring an image with a large depth of field, only in-focus regions are extracted from a plurality of images, and composition of the extracted regions is performed. In the endoscope according to the present embodiment, it is possible to reduce a difference in brightness and/or a difference in tone in a plurality of images. Accordingly, it is possible to reduce unevenness in brightness and/or a difference in tone in the composite image.

Moreover, in a method for improving the color reproducibility of the image, image composition using two images is performed. When a difference in brightness and a difference in tone occurs in two optical images, a difference in brightness and a difference in tone occurs also in two images acquired by imaging. In the endoscope according to the present embodiment, it is possible to reduce a difference in brightness and a difference in tone, even when a difference in brightness and a difference in tone occurs in a plurality of images. Accordingly, it is possible to further improve color reproducibility of the composite image.

In the image composition processor 33, first, contrast is compared using two images. This comparison is performed on each of the spatially equal pixel regions in the two images. Thereafter, the pixel region with the relatively high contrast is selected. Thereafter, one image is generated using the selected pixel region. As just described, one composite image is generated from two images. When a difference in contrast between two images is small, it suffices to generate a composite image after performing composite image processing to provide each of the images with a predetermined weight and add the weight to the images.

The rear-stage image processor 34 performs image processing, such as edge enhancement and gamma correction, on the composite image. The image output unit 35 outputs the image-processed image to the image display device 5.

In the light control unit 36, a light control signal to control brightness of light to the standard brightness is generated from the image read with the image reader 31. The light control signal is output to the diaphragm driving unit 14 of the light source 3. The diaphragm driving unit 14 regulates the opening quantity of the diaphragm 12 so as to maintain the standard brightness in accordance with the light control signal.

Figure 8:
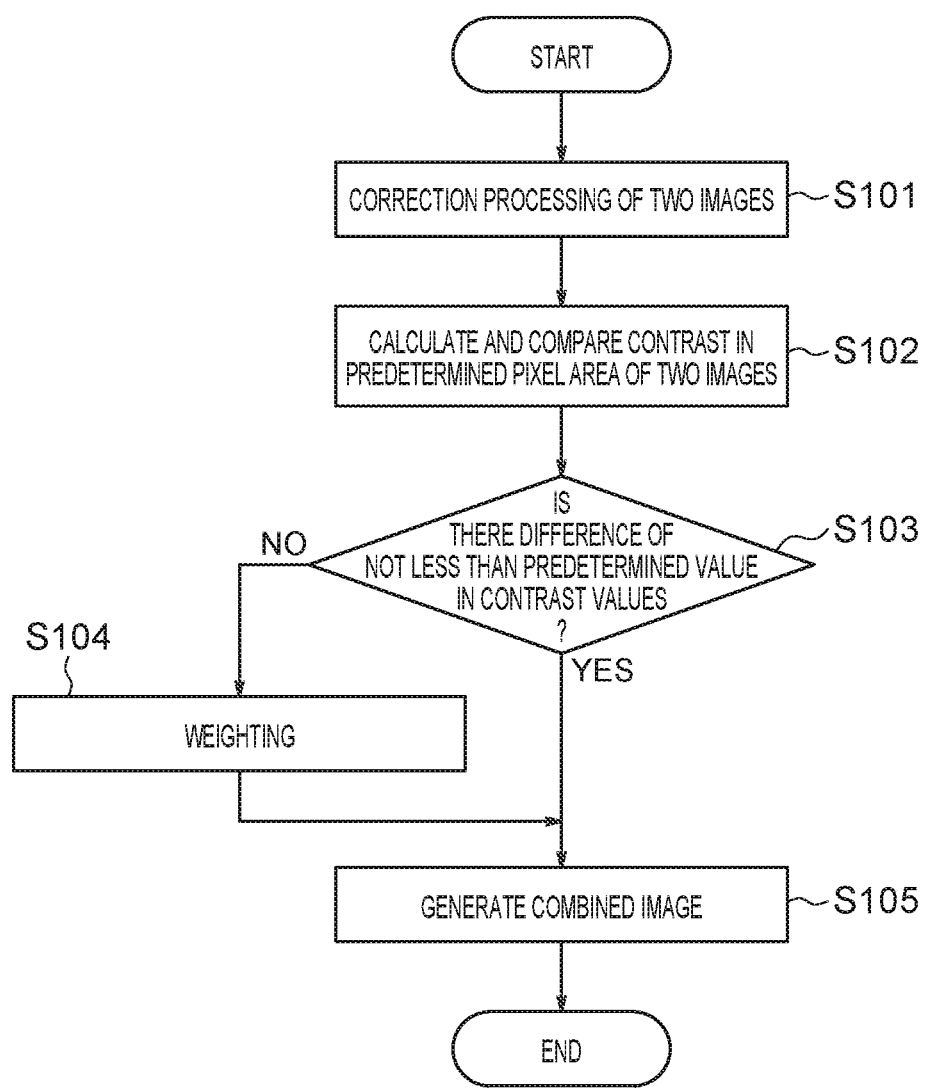
FIG. 8 is a flowchart showing a flow in a case of combining two optical images in the endoscope system according to the embodiment.

Next, in the present embodiment, a flow in a case of combining two optical images will be described below according to a flowchart in FIG. 8.

An image related to the far-point image and an image related to the near-point image with a different focus are acquired in the image sensor 122. At step S101, the two images which are the near-point image and the far-point image, are subjected to correction processing. In other words, according to correction parameters that have been set in advance, correction of two images is carried out such that the relative position, the relative angle, and the relative magnification of each optical image of the two images becomes substantially same. This correction processing is carried out in the image correction processor 32. Images after correction are output to the image composition processor 33. The brightness and color of the two images may be corrected according to the requirement.

At step S102, the image composition processor 33 synthesizes the two images subjected to the correction processing. In other words, for the pixel area corresponding to each of the far-point image and the near-point image, a contrast value is calculated, and the contrast values are compared.

At step S103, a judgment of whether or not there is a difference in the contrast values that have been compared is made. In a case in which there is a difference in the contrast, the process advances to step S105. At step S105, the image combining is carried out. In a case in which there is a difference in the contrast, an area with a high contrast value is selected, and the images are combined.

In a case in which there is no difference in the contrast or in a case in which the difference in the contrast is small, the process advances to step S104.

In a case in which the difference in the contrast values is small or in a case in which the contrast values are almost same, it is necessary to make a judgment which to select between the two images which are the far-point image and the near-point image. Wrong choice of the selection becomes a cause of unstable processing. For instance, in a case in which a selected image includes a fluctuation in a signal such as noise, a discontinuous area occurs in the combined image or a problem such that an object image which is resolved originally becomes blurred occurs.

Therefore, the process advances to step S104 and the weighting is carried out. At step S104, in the pixel area in which the contrast is compared, in a case in which the contrast values for the two images which are the far-point image and the near-point image almost same, the weighting is carried out. Moreover, the instability of the image selection is eliminated by carrying out an addition processing of images subjected to weighting at the subsequent step S105.

In such manner, according to the present embodiment, in both the close observation and the distant observation, it is possible to acquire an image in which the depth of field has been widened, while preventing the blurring of the optical image and the occurrence of the discontinuous area in the combined image due to noise.

FIG. 9 is a diagram showing an image-formation state in a case in which an image is formed on an image sensor after reflection for odd number of times by the polarization beam splitter 121. In a case of the abovementioned polarization beam splitter 121 in FIG. 8, an optical image is formed on the image sensor 122 after one reflection or in other words after reflection for the odd number of times. Consequently, one of the two images assume an image-formation state (mirror image) as shown in FIG. 8, and an image processing in which an image direction is made to coincide by inverting the mirror image in the image processor 30, is carried out.

Since correction of the mirror image by an optical reflection for the even number of times may lead to making the objective optical system large-size and the cost of the prism high, it is preferable to carry out the correction of the mirror image by reflection for the odd number of times by inverting the mirror image in the image correction processing section 32.

In a case in which the image sensor 122 has a shape which is long in a longitudinal direction of the endoscope, it is preferable to rotate the combined image appropriately up on taking into consideration an aspect ratio of the image display device 5.

Next, an objective optical system in an endoscope according to an example will be described below.

Figure 10A:
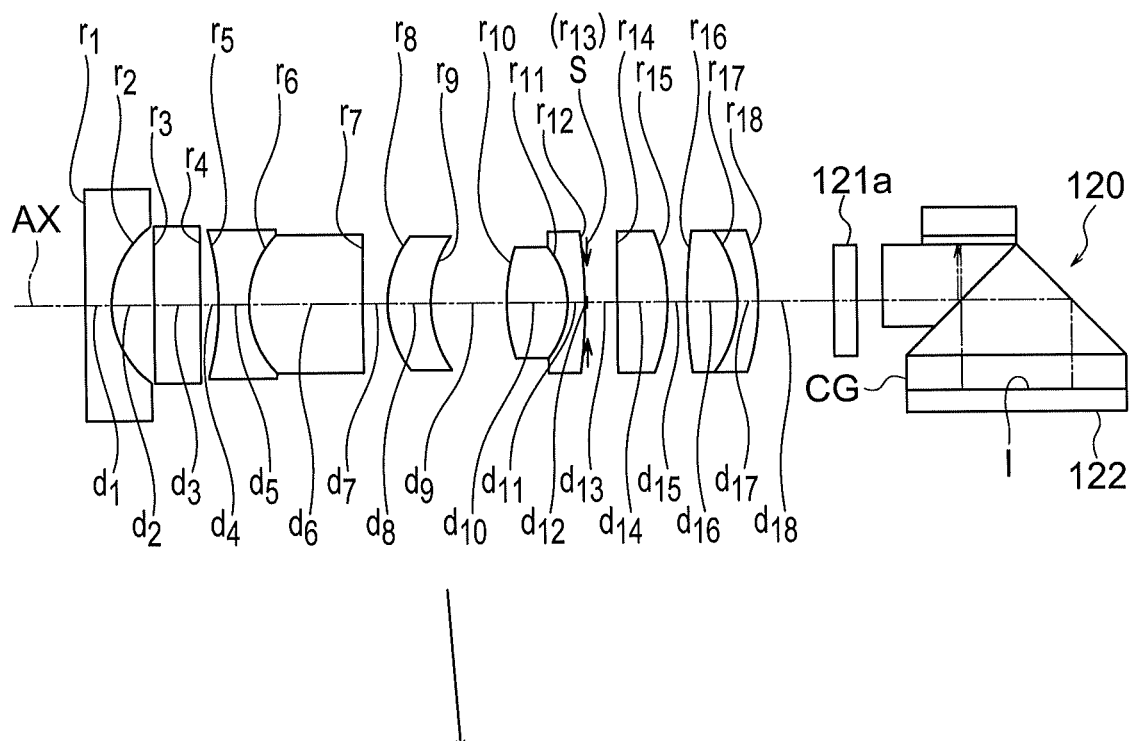
FIG. 10A and FIG. 10B are cross-sectional views showing an arrangement of an objective optical system, an optical-path splitter, and an image sensor in an endoscope system according to an example 1, where.
Figure 10B:
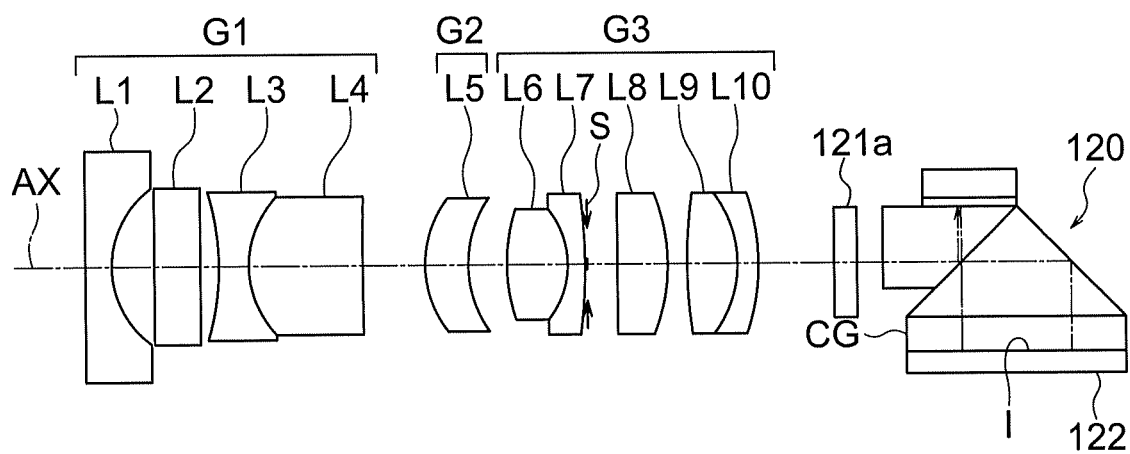

FIG. 10A and FIG. 10B are cross-sectional views showing an arrangement of an objective optical system, a λ/4 wavelength plate, an optical-path splitter, and an image sensor. Here, FIG. 10A is a cross-sectional view in a normal observation state (an object point at a long distance) and FIG. 10B is a cross-sectional view in a close observation state (an object point at a short distance).

The objective optical system of the present example includes in order from an object side, a first lens group G1 having a negative refractive power, a second lens group G2 having a positive refractive power, and a third lens group G3 having a positive refractive power. Moreover, an aperture stop S is disposed in the third lens group G3. The second lens group G2 moves toward an image side on an optical axis AX and corrects a variation in a focal position due to a change from the normal observation state to the close observation state.

The first lens group G1 includes in order from the object side, a planoconcave negative lens L1 having a flat surface directed toward the object side, a plane parallel plate L2, a biconcave negative lens L3, and a positive meniscus lens L4 having a convex surface directed toward the image side. Here, the biconcave negative lens L3 and the positive meniscus lens L4 are cemented. The second lens group G2 includes a positive meniscus lens L5 having a convex surface directed toward the object side. The third lens group G3 includes in order from the object side, a biconvex positive lens L6, a negative meniscus lens L7 having a convex surface directed toward the image side, the aperture stop S, a biconvex positive lens L8, a biconvex positive lens L9, and a negative meniscus lens L10 having a convex surface directed toward the image side. Here, the biconvex positive lens L6 and the negative meniscus lens L7 are cemented. The biconvex positive lens L9 and the negative meniscus lens L10 are cemented.

The abovementioned optical-path splitter 120 is disposed on the image side of the third lens group G3. An optical path is bent at a prism in the optical system. The plane parallel plate L2 is a filter having applied thereto a coating for cutting off light of specific wavelengths such as 1060 nm of YAG (yttrium aluminum garnet) laser, 810 nm of semiconductor laser, or light of infrared region. Here, I is an image forming surface (image pickup surface).

The λ/4 wavelength plate 121*a* is disposed in an optical path to the optical-path splitter 120 on the image side of the third lens unit G3.

Numerical data of each example is shown below. Regarding symbols, r denotes a radius of curvature of each lens surface, d denotes a distance between lens surfaces, ne denotes a refractive index for an e-line of each lens, νe denotes Abbe's number for each lens, FNO denotes an F-number, and ω denotes a half angle of view. Moreover, a back focus fb is a distance from an optical surface nearest to image up to a paraxial image plane expressed upon being subjected to air conversion. A total length TL is a length obtained by adding the back focus to a distance (not subjected to air conversion) from a lens surface nearest to object up to an optical surface nearest to image. A stop is an aperture stop.

EXAMPLE 1

Unit mm
Surface data

| Surface no. | r | d | ne | νe |
|---|---|---|---|---|
| 1 | ∞ | 0.49 | 1.88815 | 40.52 |
| 2 | 1.812 | 0.79 | | |
| 3 | ∞ | 0.84 | 1.52300 | 66.3 |
| 4 | ∞ | 0.34 | | |
| 5 | −4.881 | 0.56 | 1.88815 | 40.52 |
| 6 | 1.866 | 2.13 | 1.85504 | 23.59 |
| 7 | 77.332 | Variable | | |
| 8 | 2.010 | 0.81 | 1.48915 | 70.04 |
| 9 | 2.149 | Variable | | |
| 10 | 3.354 | 1.13 | 1.65222 | 33.53 |
| 11 | −1.665 | 0.32 | 2.01169 | 28.07 |
| 12 | −9.987 | 0.04 | | |
| 13 (Stop) | ∞ | 0.56 | | |
| 14 | 512.363 | 0.95 | 1.70442 | 29.89 |
| 15 | −3.552 | 0.36 | | |
| 16 | 9.128 | 0.94 | 1.48915 | 70.04 |
| 17 | −2.180 | 0.39 | 1.93429 | 18.74 |
| 18 | −4.093 | 4.59 | | |
| 19 (Imaging pickup surface) | ∞ | | | |

Various data

| | Normal observation state | Close observation state |
|---|---|---|
| f | 1.00 | 1.01 |
| FNO. | 3.58 | 3.53 |
| 2ω | 144.9 | 139.4 |
| fb (in air) | 4.59 | 4.59 |
| TL (in air) | 17.15 | 17.05 |
| d7 | 0.47 | 1.20 |
| d9 | 1.43 | 0.70 |

Group focal length

First group f1 = −1.12
Second group f2 = 21.78
Third group f3 = 3.51

Conditional expression (1) ΔL × npbs/Dy
(2) d/|Δn|
Δn = ne−no (difference between a refractive index of the normal light and the extraordinary light for an e-line),
$LiNbO_3$ has a negative birefringence and $YVO_4$ has a positive birefringence.

| | Example1 | Example2 | Example3 |
|---|---|---|---|
| (1) | 0.067 | 0.047 | 0.121 |
| (2) | 4.546 | 0.865 | 0.865 |
| Crystal material | $LiNbO_3$ | $YVO_4$ | $YVO_4$ |
| d | 0.4 | 0.2 | 0.2 |
| Δn | −0.08798 | 0.23122 | 0.23122 |
| ΔL1 | 0.05 | 0.05 | 0.1 |

-continued

|     |         |         |         |
|-----|---------|---------|---------|
| ΔL2 | −0.0073 | 0.0102  | 0.0102  |
| ΔL  | 0.0573  | 0.0398  | 0.0898  |
| npbs| 1.64129 | 1.64129 | 1.75844 |
| Dy  | 1.4     | 1.4     | 1.3     |

Example4

| (1) | 0.012 |
|-----|-------|
| (2) | 5.683 |

| Crystal material | LiNbO$_3$ |
|------------------|-----------|
| d   | 0.5      |
| Δn  | −0.08798 |
| ΔL1 | 0.01     |
| ΔL2 | −0.0092  |
| ΔL  | 0.0192   |
| npbs| 1.75844  |
| Dy  | 2.8      |

|     | Example5 | Example6 |
|-----|----------|----------|
| (1) | 0.018    | 0.15     |
| (2) | 0.086    | 0.432    |

| Crystal material | YVO$_4$ | YVO$_4$ |
|------------------|---------|---------|
| d   | 0.02    | 0.1     |
| Δn  | 0.23122 | 0.23122 |
| ΔL1 | 0.01    | 0.1     |
| ΔL2 | 0.001   | 0.0051  |
| ΔL  | 0.009   | 0.0949  |
| npbs| 1.51825 | 1.64129 |
| Dy  | 0.76    | 1.04    |

Characteristics of examples from the example 1 to the example 6 will be described below.

(A) The example 1 is a typical example in which LiNbO$_3$ is used as a material of the λ/4 wavelength plate.

(B) The example 2 is an example in which the λ/4 wavelength plate is thinned by using YVO$_4$ having a high birefringence for a material of the λ/4 wavelength plate.

(C) The example 3 is an example in which an extinction ratio is improved by thinning the λ/4 wavelength plate by using YVO$_4$ for the material of the λ/4 wavelength plate, and by making the refractive index of the polarization beam splitter high by using S-YGH51 (manufactured by OHARA Corporation) for the glass material of the polarization beam splitter. Moreover, in the example 3, by allowing the sliding amount (amount of adjustment of the manufacturing error) to be close to the upper limit of conditional expression (1), and instead, by relaxing a component tolerance of the polarization beam splitter, the price is lowered.

(D) In the example 4, LiNbO$_3$ is used for the material of the λ/4 wavelength plate, and by satisfying the upper limit value of conditional expression (2), the λ/4 wavelength plate is thickened in order to make it easy to handle. Moreover, the example 4 is an example in which the extinction ratio is improved by using S-YGH51 (manufactured by OHARA Corporation) for the glass material of the polarization beam splitter similarly as in the example 3. Moreover, in the example 4, the component tolerance of the polarization beam splitter is made highly accurate, and the sliding amount necessary for the adjustment is made small closer to the lower limit of conditional expression (1). Therefore, even when the number of pixels of the image sensor is made large, the size of the front-end portion of the endoscope does not become larger than necessary.

(E) The example 5 is an example in which a nasal endoscope in which a small-size image sensor has been used is envisioned. S-BSL7 (manufactured by OHARA Corporation) is used for the polarization beam splitter, and small-sizing of Dy of up to less than 0.76 to 1 mm with the small-sizing of endoscope is achieved. Moreover, in addition to the small-sizing of the polarization beam splitter, the component tolerance thereof is also made highly accurate. Furthermore, the example 5 is an example in which thinning the λ/4 wavelength plate up to the lower limit value of conditional expression (2) by using YVO$_4$ for the material of the λ/4 wavelength plate has contributed to small-sizing of the size of the front-end portion of endoscope.

(F) Example 6 is an example in which, with regard to the thinning processing of the λ/4 wavelength plate and the processing of the polarization beam splitter, the degree of processing is relaxed up to the upper limit of conditional expression (1), and the manufacturing cost is lowered. Moreover, the example 6 is an example in which, the relaxation of the degree of difficulty of processing, lowering of the manufacturing cost, as well as small-sizing of the front-end portion of endoscope are targeted similarly as in the example 5.

The abovementioned endoscope may satisfy the plurality of arrangements simultaneously. Satisfying the plurality of arrangements simultaneously is preferable for achieving a favorable endoscope. Moreover, a combination of the preferable arrangements is arbitrary. Furthermore, regarding each conditional expression, an upper limit value or a lower limit value of a numerical range of a further restricted conditional expression may be restricted.

Various embodiments of the present invention have been described heretofore. However, the present invention is not restricted to the embodiments described heretofore, and embodiments in which arrangements of these embodiments are combined appropriately without departing from the scope of the present invention are also within the scope of the present invention.

As described heretofore, the present invention is useful for an endoscope, a method for adjustment of endoscope, and an image pickup apparatus which enable to correct the shift in the image forming position occurred due to birefringence with a compact arrangement, while achieving an adequate depolarization effect.

The present invention shows an effect that it is possible to provide an endoscope, a method for adjustment of endoscope, and an image pickup apparatus which enable to correct the shift in the image forming position occurred due to birefringence, with a compact arrangement, while achieving an adequate depolarization effect.

What is claimed is:

1. An endoscope, comprising in order from an object side:
   an objective optical system including at least one lens group; and
   an optical-path splitter which splits light from the objective optical system into a first optical path and a second optical path,
   wherein:
   a λ/4 wavelength plate made of a birefringent material is disposed in an optical path between the objective optical system and the optical-path splitter, where λ denotes a wavelength,
   the optical-path splitter includes in order from the object side, a first prism and a second prism,
   the optical-path splitter has a beam splitting surface at which the first prism and the second prism are brought into close contact,
   the optical-path splitter splits light at the beam splitting surface into the first optical path through which P-polarized light is transmitted and the second optical path through which S-polarized light is reflected, and
   the first prism and the second prism are slid relative to one another along the beam splitting surface to adjust an optical path length of the first optical path from the beam splitting surface to an image forming surface of an image sensor and an optical path length of the second optical path from the beam splitting surface to the image forming surface of the image sensor, and the first prism and the second prism are disposed at positions of cancelling an amount of shift in a focusing position of extraordinary light exiting the λ/4 wavelength plate and that is split to the first optical path and a focusing position of ordinary light exiting the λ/4 wavelength plate and that is split to the second optical path, the shift in the focusing position of the extraordinary light and the focusing position of the ordinary light occurring due to the λ/4 wavelength plate having birefringence, and satisfy the following conditional expressions (1) and (2), $0.01 < \Delta L \times npbs/Dy \leq 0.15$ (1)

$0.09 \leq d/|\Delta n| \leq 5.7$ (2) (unit mm)

where,
   ΔL is an air conversion length and denotes an amount of adjustment of a difference in the optical path length of the second optical path and the optical path length of the first optical path in the optical-path splitter, and here $\Delta L = |\Delta L1 - \Delta L2|$, where ΔL1 is an air conversion length and denotes a difference in the optical path length of the first optical path and the optical path length of the second optical path that occurs due to a manufacturing error of the optical-path splitter, ΔL2 is an air conversion length and denotes the amount of shift in the focusing position of the extraordinary light and the focusing position of the ordinary light that occurs due to the λ/4 wavelength plate,
   npbs denotes a refractive index for an e-line of the optical-path splitter,
   Dy denotes a dimension of the optical-path splitter in a direction that is orthogonal to an optical axis of the objective optical system, after the first prism and the second prism are slid relative to one another along the beam splitting surface to adjust the optical path length of the first optical path and the optical path length of the second optical path,
   d denotes a thickness of the λ/4 wavelength plate, and
   Δn denotes a birefringence for an e-line of the λ/4 wavelength plate.

2. The endoscope according to claim 1, wherein a birefringent material of the λ/4 wavelength plate is one of $LiNbO_3$, $YVO_4$, calcite, and α-BBO.

3. The endoscope according to claim 1, wherein the endoscope satisfies the following conditional expression (1)'

$0.047 \leq \Delta L \times npbs/Dy \leq 0.15$ (1)'.

4. The endoscope according to claim 1, wherein the endoscope satisfies the following conditional expression (1)"

$0.047 \leq \Delta L \times npbs/Dy \leq 0.121$ (1)".

5. The endoscope according to claim 1, wherein the endoscope satisfies the following conditional expression (1)'''

$0.067 \leq \Delta L \times npbs/Dy \leq 0.121$ (1)'''.

6. The endoscope according to claim 1, wherein the endoscope satisfies the following conditional expression (2)'

$0.432 \leq d/|\Delta n| \leq 5.7$ (2)'.

7. The endoscope according to claim 1, wherein the endoscope satisfies the following conditional expression (2)"

$0.432 \leq d/|\Delta n| \leq 4.546$ (2)".

8. The endoscope according to claim 1, wherein the endoscope satisfies the following conditional expression (2)'''

$0.716 \leq d/|\Delta n| \leq 4.546$ (2)'''.

9. A method for adjustment of an endoscope,
   wherein the endoscope includes in order from an object side,
   an objective optical system including at least one lens group,
   an optical-path splitter which splits light from the objective optical system into a first optical path and a second optical path, and
   a λ/4 wavelength plate made of a birefringent material is disposed in an optical path between the objective optical system and the optical-path splitter, where λ denotes a wavelength,
   wherein:
   the optical-path splitter includes in order from the object side, a first prism and a second prism,
   the optical-path splitter has a beam splitting surface at which the first prism and the second prism are brought into close contact, and
   the optical-path splitter splits the light at the beam splitting surface, into the first optical path through which P-polarized light is transmitted and the second optical path through which S-polarized light is reflected, wherein the method comprises:

adjusting an optical path length of the first optical path from the beam splitting surface to an image forming surface of an image sensor and an optical path length of the second optical path from the beam splitting surface to the image forming surface of the image sensor by sliding the first prism and the second prism relative to one another along the beam splitting surface to adjust a manufacturing error of the optical-path splitter, and to cancel an amount of shift in a focusing position of extraordinary light exiting the λ/4 wavelength plate and that is split to the first optical path and a focusing position of ordinary light exiting the λ/4 wavelength plate and that is split to the second optical path, the shift in the focusing position of the extraordinary light and the focusing position of the ordinary light occurring due to the λ/4 wavelength plate having birefringence, wherein:

the following conditional expressions (1) and (2) are satisfied $$0.01 < \Delta L \times npbs/Dy \leq 0.15 \quad (1)$$

$$0.09 \leq d/|\Delta n| \leq 5.7 \quad (2) \text{ (unit mm)}$$

where,

ΔL is an air conversion length and denotes an amount of adjustment of a difference in the optical path length of the second optical path and the optical path length of the first optical path in the optical-path splitter, and here $$\Delta L = |\Delta L1 - \Delta L2|, \text{ where}$$

ΔL1 is an air conversion length and denotes a difference in the optical path length of the first optical path and the optical path length of the second optical path that occurs due to the manufacturing error of the optical-path splitter, ΔL2 is an air conversion length and denotes the amount of shift in the focusing position of the extraordinary light and the focusing position of the ordinary light that occurs due to the λ/4 wavelength plate, npbs denotes a refractive index for an e-line of the optical-path splitter, Dy denotes a dimension of the optical-path splitter in a direction that is orthogonal to an optical axis of the objective optical system, after the first prism and the second prism are slid relative to one another along the beam splitting surface to adjust the optical path length of the first optical path and the optical path length of the second optical path, d denotes a thickness of the λ/4 wavelength plate, and Δn denotes a birefringence for an e-line of the λ/4 wavelength plate.

10. The method for adjustment of endoscope according to claim 9, wherein the following conditional expression (1)' is satisfied $$0.047 \leq \Delta L \times npbs/Dy \leq 0.15 \quad (1)'$$

11. The method for adjustment of endoscope according to claim 9, wherein the following conditional expression (1)'' is satisfied $$0.047 \leq \Delta L \times npbs/Dy \leq 0.121 \quad (1)''$$

12. The method for adjustment of endoscope according to claim 9, wherein the following conditional expression (1)''' is satisfied $$0.067 \leq \Delta L \times npbs/Dy \leq 0.121 \quad (1)'''$$

13. The method for adjustment of endoscope according to claim 9, wherein the following conditional expression (2)' is satisfied $$0.432 \leq d/|\Delta n| \leq 5.7 \quad (2)'$$

14. The method for adjustment of endoscope according to claim 9, wherein the following conditional expression (2)'' is satisfied $$0.432 \leq d/|\Delta n| \leq 4.546 \quad (2)''$$

15. The method for adjustment of endoscope according to claim 9, wherein the following conditional expression (2)''' is satisfied $$0.716 \leq d/|\Delta n| \leq 4.546 \quad (2)'''$$

16. An image pickup apparatus including an image sensor, the image pickup apparatus comprising, in order from an object side:

an objective optical system including at least one lens group; and an optical-path splitter which splits light from the objective optical system into a first optical path and a second optical path, wherein:

a λ/4 wavelength plate made of a birefringent material is disposed in an optical path between the objective optical system and the optical-path splitter, where λ denotes a wavelength, the optical-path splitter includes in order from the object side, a first prism and a second prism, the optical-path splitter has a beam splitting surface at which the first prism and the second prism are brought into close contact, the optical-path splitter splits the light at the beam splitting surface, into the first optical path through which P-polarized light is transmitted and the second optical path through which S-polarized light is reflected, and the first prism and the second prism are slid relative to one another along the beam splitting surface to adjust an optical path length of the first optical path from the beam splitting surface to an image forming surface of an image sensor and an optical path length of the second optical path from the beam splitting surface to the image forming surface of the image sensor, and are disposed at positions of cancelling an amount of shift in a focusing position of extraordinary light exiting the λ/4 wavelength plate and that is split to the first optical path and a focusing position of ordinary light exiting the λ/4 wavelength plate and that is split to the second optical path, the shift in the focusing position of the extraordinary light and the focusing position of the ordinary light occurring due to the λ/4 wavelength plate having birefringence, and the following conditional expressions (1) and (2) are satisfied $$0.01 < \Delta L \times npbs/Dy \leq 0.15 \quad (1)$$

$$0.09 \leq d/|\Delta n| \leq 5.7 \quad (2) \text{ (unit mm)}$$

where,

ΔL is an air conversion length and denotes an amount of adjustment of a difference in the optical path length of the second optical path with respect to the first optical path in the optical-path splitter, and here $$\Delta L = |\Delta L1 - \Delta L2|, \text{ where}$$

ΔL1 is an air conversion length and denotes a difference in the optical path length of the first optical path and the optical path length of the second optical path that occurs due to a manufacturing error of the optical-path splitter, ΔL2 is an air conversion length and denotes the amount of shift in the focusing position of the extraordinary light and the focusing position of the ordinary light that occurs due to the λ/4 wavelength plate, npbs denotes a refractive index for an e-line of the optical-path splitter, Dy denotes a dimension of the optical-path splitter in a direction that is orthogonal to an optical axis of the objective optical system, after the first prism and the second prism are slid relative to one another along the beam splitting surface to adjust the optical path length of the first optical path and the optical path length of the second optical path, d denotes a thickness of the λ/4 wavelength plate, and Δn denotes a birefringence for an e-line of the λ/4 wavelength plate.

17. The image pickup apparatus according to claim 16, wherein the following conditional expression (1)' is satisfied $$0.047 \leq \Delta L \times npbs/Dy \leq 0.15 \tag{1}'$$

18. The image pickup apparatus according to claim 16, wherein the following conditional expression (1)'' is satisfied $$0.047 \leq \Delta L \times npbs/Dy \leq 0.121 \tag{1}''$$

19. The image pickup apparatus according to claim 16, wherein the image pickup apparatus satisfies the following conditional expression (2)' is satisfied $$0.432 \leq d/|\Delta n| \leq 5.7 \tag{2}'$$

20. The image pickup apparatus according to claim 16, wherein the following conditional expression (2)'' is satisfied.

$$0.432 \leq d/|\Delta n| \leq 4.546 \tag{2}''$$

\* \* \* \* \*